US010136636B2

(12) United States Patent
Lai et al.

(10) Patent No.: US 10,136,636 B2
(45) Date of Patent: Nov. 27, 2018

(54) VITRIFICATION OF BIOLOGICAL MATERIAL

(71) Applicant: THE REGENTS OF THE UNIVERSITY OF MICHIGAN, Ann Arbor, MI (US)

(72) Inventors: David Lai, Ann Arbor, MI (US); Shuichi Takayama, Ann Arbor, MI (US); Gary D. Smith, Ann Arbor, MI (US); Jun Ding, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/029,353

(22) PCT Filed: Oct. 14, 2014

(86) PCT No.: PCT/US2014/060389
§ 371 (c)(1),
(2) Date: Apr. 14, 2016

(87) PCT Pub. No.: WO2015/057641
PCT Pub. Date: Apr. 23, 2015

(65) Prior Publication Data
US 2016/0270388 A1  Sep. 22, 2016

Related U.S. Application Data (60) Provisional application No. 61/891,207, filed on Oct. 15, 2013.

(51) Int. Cl.
*A01N 1/02* (2006.01)
*C12N 1/04* (2006.01)
(Continued)

(52) U.S. Cl.
CPC ......... *A01N 1/0252* (2013.01); *A01N 1/0221* (2013.01); *A01N 1/0242* (2013.01); (Continued)

(58) Field of Classification Search
CPC .. A01N 1/0221; A01N 1/0242; A01N 1/0252; A01N 1/0257; B01L 2200/0647; (Continued)

(56) References Cited

U.S. PATENT DOCUMENTS 7,144,616 B1   12/2006   Unger et al.
7,601,270 B1   10/2009   Unger et al.
(Continued)

FOREIGN PATENT DOCUMENTS

WO   2011146998 A1   12/2011

OTHER PUBLICATIONS

Search Report of Corresponding International Application No. PCT/US2014/060389, dated Mar. 26, 2015, 17 pages.
(Continued)

*Primary Examiner* — Michael L Hobbs
(74) *Attorney, Agent, or Firm* — Casimir Jones, S.C.; Tanya A. Arenson (57) ABSTRACT

Microfluidic cryopreservation technology is provided and particularly, but not exclusively, devices, systems, and methods for cryopreservation of biological materials such as oocytes, zygotes, and embryos. The present microfluidic devices and related systems and methods are configured to maintain biological material in a housing chamber when subjected to a constant volumetric flow of fluid of changing fluid density.

15 Claims, 4 Drawing Sheets

(51) Int. Cl.
 B01L 7/00 (2006.01)
 B01L 3/00 (2006.01)
(52) U.S. Cl.
 CPC ........ A01N 1/0257 (2013.01); B01L 3/50273 (2013.01); B01L 3/502715 (2013.01); B01L 7/50 (2013.01); *B01L 3/5027* (2013.01); *B01L 2200/0647* (2013.01); *B01L 2300/0867* (2013.01); *B01L 2300/0883* (2013.01); *B01L 2300/1894* (2013.01); *B01L 2400/0478* (2013.01)
(58) Field of Classification Search
 CPC ..... B01L 2300/0867; B01L 2300/0883; B01L 2300/1894; B01L 2400/0478; B01L 3/5027; B01L 3/502715; B01L 3/50273; B01L 7/50
 See application file for complete search history.

(56) References Cited

U.S. PATENT DOCUMENTS

| | | | |
|---|---|---|---|
| 2002/0029814 A1 | 3/2002 | Unger et al. | |
| 2008/0229609 A1* | 9/2008 | Bronshtein | A01N 1/0284 34/287 |
| 2008/0277005 A1 | 11/2008 | Unger et al. | |
| 2011/0250690 A1* | 10/2011 | Craig | A01N 1/02 435/404 |
| 2012/0152740 A1 | 6/2012 | Kim et al. | |
| 2012/0251999 A1 | 10/2012 | Demirci et al. | |
| 2013/0280725 A1* | 10/2013 | Ismagilov | B01L 3/5027 435/6.12 |

OTHER PUBLICATIONS

Beier et al., "Effective surface-based cryopreservation of human embryonic stem cells by vitrification." Cryobiology. Dec. 2011;63(3):175-85.
Chian et al., "High survival rate of bovine oocytes matured in vitro following vitrification." J Reprod Dev. Dec. 2004;50(6):685-96.
Fu et al., "Buckling of yeast modeled as viscoelastic shells with transverse shearing" Archive of Applied Mechanics, Jan. 2012, vol. 82, Issue 1, pp. 69-77.
Kargol et al., "Membrane Transport Generated by the Osmotic and Hydrostatic Pressure. Correlation Relation for Parameters L(p), σ, and ω." J Biol Phys. Dec. 2000;26(4):307-20.
Kargol et al., "Mechanistic Formalism for Membrane Transport Generatedby Osmotic and Mechanical Pressure" Gen. Physiol. Biophys. (2003), 22, 51-68.
Kedem et al., "A Physical Interpretationof the Phenomenological Coefficientsof Membrane Permeability" The Journal of General Physiology, 1961, p. 143-79.
Kedem et al., "Thermodynamic analysis of the permeability of biological membranes to non-electrolytes." Biochim Biophys Acta. Feb. 1958;27(2):229-46.
Kuleshova et al., "Sugars exert a major influence on the vitrification properties of ethylene glycol-based solutions and have low toxicity to embryos and oocytes." Cryobiology. Mar. 1999;38(2):119-30.
Melin et al., "Microfluidic large-scale integration: the evolution of design rules for biological automation." Annu Rev Biophys Biomol Struct. 2007;36:213-31.
Miyake et al., "An actin barrier to resealing." J Cell Sci. Oct. 2001;114(Pt 19):3487-94.
Paynter et al., "Temperature dependence of Kedem-Katchalsky membrane transport coefficients for mature mouse oocytes in the presence of ethylene glycol." Cryobiology. Sep. 1999;39(2):169-76.
Prentice-Biensch et al., "Vitrification of immature bovine cumulus-oocyte complexes: effects of cryoprotectants, the vitrification procedure and warming time on cleavage and embryo development." Reprod Biol Endocrinol. Sep. 6, 2012;10:73.
Quake et al., "From micro- to nanofabrication with soft materials." Science. Nov. 24, 2000;290(5496):1536-40.
Ragoonanan et al., "Response of the cell membrane-cytoskeleton complex to osmotic and freeze/thaw stresses." Cryobiology. Dec. 2010;61(3):335-44.
Rall et al., "Ice-free cryopreservation of mouse embryos at −196 degrees C by vitrification." Nature. Feb. 14-20, 1985;313(6003):573-5.
Roy et al., "Embryo vitrification using a novel semiautomated closed system yields in vitro outcomes equivalent to the manualCryotop method" Human Reproduction, vol. 0, No. 0 pp. 1-8, 2014.
Tsang et al., "Cryopreservation of mammalian embryos: Advancement of putting life on hold." Birth Defects Res C Embryo Today. Sep. 2010;90(3):163-75.

* cited by examiner

VITRIFICATION OF BIOLOGICAL MATERIAL

CROSS REFERENCE TO RELATED APPLICATION

The present application is a 371 U.S. National Phase Entry of pending International Application No. PCT/US2014/060389, filed Oct. 14, 2014, which claims priority to U.S. Provisional Patent Application Ser. No. 61/891,207, filed Oct. 15, 2013, the disclosure of which is herein incorporated by reference in their entireties.

FIELD OF INVENTION

Provided herein is technology relating to cryopreservation and particularly, but not exclusively, to devices, systems, and methods for cryopreservation of biological materials such as oocytes, zygotes, and embryos.

BACKGROUND

Assisted reproductive techniques (ART) such as in vitro fertilization (IVF) often require the preservation of oocytes and zygotes. Currently, approximately 1.5 million assisted reproductive procedures are performed worldwide. According to the American Society of Reproductive Medicine, IVF procedures cost a patient over $12,000 on average. Thus, increasing the number and quality of preserved oocytes and embryos would improve the success of assisted reproductive techniques such as IVF and reduce patient costs. In addition, it has been recently estimated that 1 in every 47 women will develop some form of invasive cancer within their reproductive age. As efforts in the scientific community continue to improve cancer survival, there is an ever-growing demand to preserve oncofertility for young women of reproductive age. The approaches for addressing both of these issues involve cryopreservation of oocytes or zygotes, which typically involves one of two conventional methods: slow-rate freezing or vitrification. In recent years, vitrification has provided increased cryosurvival of oocytes and zygotes as measured by a lower percentage of cell death post-warming and better time efficiency than other methods.

Vitrification is a process of freezing used to preserve oocytes (e.g., eggs) and embryos used for assisted reproductive therapies (see, e.g., Rall & Fahy (1985) *Nature* 313: 573-75). During conventional methods of manual vitrification, the oocytes and/or embryos are exposed to solutions with increasing concentrations of cryopreservative agents that prevent the formation of ice crystals (id). However, the viability of the oocytes and embryos is reduced as a result of the osmotic shock produced by the sudden volume change due to loss of water caused by these agents (Prentice-Biensch et al (2012) *Reproductive Biology and Endocrinology* 10:73).

Due to the thermodynamics of the vitrification process, vitrification solutions comprising high concentrations of cryoprotectant agents (CPA) are typically used to avoid ice formation during the non-equilibrium phase change from liquid to glass phase. As a result of their large size and low surface-to-volume ratio, transfer of oocytes and zygotes from culture media (CM) conditions at physiologic osmolality to a vitrification solution (VS) with high osmolality produces deleterious osmotic stress on the oocytes and zygotes. In addition, while the increase in osmolality produced by cryoprotectant agents is thermodynamically favorable for vitrification, the increase in osmolality also decreases cell volume from loss of cell liquid.

Early studies on osmotic stress indicated that at some limiting minimum cell volume, the osmotic stress becomes sufficient to cause lethal damage to cell membrane integrity. This concept of a limiting minimum cell volume has formed the basis of numerous osmotic stress studies. As a result, the conventional standard method for oocyte and zygote vitrification involves a 3-step equilibration process in which the oocytes or zygotes are manually pipetted into three subsequently higher levels of CPA concentrations. This procedure avoids sudden changes of osmolality by spreading the osmotic stress over an extended period of time and avoids the critical minimum cell volume by allowing the cell to shrink slowly and sometimes to re-expand. Further studies have shown that increasing the number of equilibration steps increases cryosurvival. However, protocols with large numbers of equilibration steps have not been clinically adopted due to the impracticality of performing many manual pipetting steps.

Accordingly, cryoprotection of biological materials such as oocytes and embryos would benefit from improved methods that decrease the osmotic shock during vitrification to increase cell health and developmental competence without increasing user involvement and accompanying user error in the process.

SUMMARY

Provided herein is technology relating to cryopreservation and particularly, but not exclusively, to devices, systems, and methods for cryopreservation of biological materials (e.g., oocytes and embryos; cells, tissues; stem cells). In particular, provided herein is technology related, in some embodiments, to a novel microfluidic cryoprotectant exchange device and related methods for vitrification of oocytes and zygotes to preserve oncofertility or stem cells and stem cell products in regenerative medicine.

Conventional cryoprotection technologies are based on osmotic stress models that associate cryosurvival with minimum cell volume. Despite the successes of these technologies, it has become evident that basing methods on minimum cell volume is insufficient as an indicator of fertility preservation for oocytes and zygotes. Accordingly, the technology provided herein controls cell shrinkage rate, provides for uniform exposure as the concentration of cryoprotectant solution is gradually changed, in addition to providing control over minimum cell volume to lower osmotic stresses contributing to sub-lethal damage.

Based on the Kedem-Katchalsky equations, a new mathematical model for predicting the association of osmotic stresses with shrinkage rate was constructed and experiments were devised to test the model's predictions. During the development of embodiments of the technology provided herein, data were collected that associated shrinkage rate with sub-lethal osmotic stress. Accordingly, embodiments of the technologies provided herein (e.g., a microfluidic device that provides for a gradual shrinkage rate not attainable with conventional manual cryoprotectant pipetting) ameliorated the effects of shrinkage rate on osmotic stress.

In particular, the experiments demonstrated that the technology increased cell health and preserved fertility as measured by developmental competence. Additional measureable indicators such as cell shape and lipid retention were predictive of the eventual developmental competence. Bovine oocytes exposed to cryoprotectants using this technology showed improved survival compared to oocytes exposed to cryoprotectants manually and experienced lower osmotic stress and demonstrated improved lipid retention and higher volumes of cellular fluids. Murine embryos vitrified using this technology showed better development than manually vitrified embryos and experienced lower osmotic stress and demonstrated a superior embryo developmental competence, improved morphology, and other improved physical characteristics. Blastocysts from embryos vitrified according to the technology were demonstrated to have similar numbers of cells as control (e.g., untreated) embryos.

The technology provides advantages in ease of operation relative to conventional (e.g., manual) technologies and has added capabilities such as real-time visualization and monitoring of an oocyte, a zygote, a stem cell, an embryo, an ovarian follicle, a embryoid body, an organoid, or a tissue, etc. during the cryopreservation process. The technology finds use in the vitrification of an oocyte, a zygote, a stem cell, an embryo, an ovarian follicle, a embryoid body, an organoid, or a tissue (e.g., mammalian (e.g., human) oocytes and/or embryos) for assisted reproduction technologies and methods used in human and veterinary contexts, e.g., to treat patients affected by infertility, fertility preservation for cancer patients, in vitro cattle production, animal breeding, etc. Moreover, the technology finds use in the cryopreservation of cells (e.g., stem cells, e.g., embryonic stem cells, adult stem cells, etc.) for many extant and emerging technologies related to cell-based (e.g., stem-cell based) therapies and regenerative medicine (see, e.g., Beier et al (2011) *Cryobiology* 63:175-85).

In particular embodiments, the technology provides a microfluidic device and associated automated methods for exposing cells (e.g., oocytes, zygotes, stem cells) to cryoprotectants in a controlled manner (e.g., to control the rate of shrinkage). In some embodiments, a microfluidic technology (e.g., devices, methods, and systems) controls the rate at which a cryopreservative is exchanged with the cellular medium such that the osmotic shock experienced by the oocyte and/or zygote is minimized and/or eliminated. In some embodiments, the cells are visualized during vitrification or warming, thus providing a technology for selecting appropriate oocytes and/or zygotes (e.g., by choosing oocytes and/zygotes having observable characteristics such as shape, size, surface features, staining patterns, etc. that are associated with increased or desirable cell health, survival, developmental competence, fertilizability, etc.). In some embodiments, methods comprise use of a vitrification solution comprising an impermeable solute (e.g., sucrose). Related system embodiments comprise a component that is a solution comprising an impermeable solute such as sucrose.

Accordingly, provided herein is technology related to a microfluidic device for the cryopreservation of a biological material, the device comprising a source of a vitrification solution comprising a continuous time-dependent cryoprotectant agent concentration and a housing chamber for exposing a biological material to the vitrification solution to cryopreserve the biological material. In some embodiments, the source of the vitrification solution comprises a serpentine mixing channel, an input for a solution comprising a cryoprotectant agent, an input for a culture medium, and a delivery channel in fluid communication with the housing chamber. In some embodiments, the vitrification solution comprises an impermeable solute. In some embodiments, the device further comprises a port for access to the housing chamber, e.g., for the loading and/or withdrawal of the biological material from the microfluidic device. In some embodiments, the device comprises a negative pressure (e.g., vacuum powered) holding channel to maintain the biological material in the housing chamber. In some embodiments, the device further comprises a vitrification solution as described herein. For example, in some embodiments, the device comprises a cryoprotectant agent having a concentration that changes as a function of time according to the technology provided herein. In some embodiments, the device comprises a biological material that is to be cryopreserved, e.g., an oocyte, a zygote, a stem cell or stem cell product (e.g., from a human (e.g., a human having cancer or infertility or needing regenerative medicine)). The technology is not limited in the material from which the device is constructed. For example, in some embodiments the device is made from (e.g., the device comprises) polydimethylsiloxane (PDMS) and in some embodiments the device is made by soft lithography techniques. Accordingly, in some embodiments the device is transparent or translucent such that the microfluidic device allows observation of a biological material contained in the microfluidic device.

The technology further provides systems the cryopreservation of a biological material, e.g., a system comprising a microfluidic device as described herein; a solution comprising a cryoprotectant agent; a syringe pump in operable fluidic communication with the input for the solution comprising the cryoprotectant agent; a syringe pump in operable fluidic communication with the input for the culture medium; and a thermodynamic heat pump to remove heat from the device and freeze biological material contained therein. In some embodiments of systems, the systems further comprise a microchip configured to execute computer instructions to control the syringe pump in operable fluidic communication with the input for the solution comprising a cryoprotectant agent and to control the syringe pump in operable fluidic communication with the input for the culture medium. In some embodiments, a rate of delivery of the solution comprising the cryoprotectant agent is controllable and the rate of delivery of the culture medium is controllable. For instance, in some embodiments, the systems comprise a computer and software to control the delivery of the components in the vitrification solution to the device and mixer. In some embodiments, the syringe pump in operable fluidic communication with the input for the solution comprising a cryoprotectant agent and the syringe pump in operable fluidic communication with the input for the culture medium provide a vitrification solution comprising a time-dependent concentration of the cryoprotectant agent.

Further embodiments relate to a method for cryopreserving a biological material, the method comprising loading a biological material into a microfluidic device; exposing the biological material to a vitrification solution having a time-dependent concentration of a cryoprotectant agent; and vitrifying the biological material. Related embodiments provide a method for the production of a cryopreserved biological material, the method comprising loading a biological material into a microfluidic device; exposing the biological material to a vitrification solution having a time-dependent concentration of a cryoprotectant agent; and vitrifying the biological material.

In some embodiments, methods comprise mixing a culture medium and a solution comprising the cryoprotectant to provide the vitrification solution. In some embodiments, methods comprise pumping a culture medium from a syringe pump and pumping a solution comprising the cryoprotectant to provide the vitrificationt solution. In particular embodiments, the vitrification solution comprises an impermeable solute. According to particular aspects of the technology, methods are provided that minimize the rate of cell shrinkage and thus minimize or eliminate the osmotic and other stresses experienced by cells during vitrification and/or freezing. According, in some embodiments methods comprise controlling the rate of cell shrinkage. In some embodiments, methods comprise visualizing or monitoring the biological material, e.g., to select at least a portion of the biological material (e.g., one or more zygotes, oocytes, embryos, cells (e.g., stem cells), etc.) based on the results of the visualizing and/or monitoring that indicates that the selected biological material has desirable characteristics (e.g., improved fertilizability, improved survival, improved developmental competence, etc.). Thus, in some embodiments methods comprise selecting at least a portion of the biological material based on the visualizing or monitoring.

The technology provides compositions, e.g., in some embodiments the technology provides a cryopreserved biological material prepared using a device, a system, or a method described herein. For example, in some embodiments the technology provides a cryopreserved biological material obtainable by a method comprising steps described herein, e.g., loading a biological material into a microfluidic device; exposing the biological material to a vitrification solution having a time-dependent concentration of a cryoprotectant agent; and vitrifying the biological material.

The biological materials, in some embodiments, have improved cell health, post-warming survival, fertility, morphology, lipid retention, and/or developmental competence relative to the biological material prepared by a manual technology. In some embodiments, the cryopreserved biological material has experienced less osmotic stress relative to the biological material prepared by a manual technology. In particular embodiments, the cryopreserved biological material is an oocyte, a zygote, an embryo, or a stem cell or stem cell product and in some embodiments the cryopreserved biological material is from a human.

Further embodiments provide a method for assisted reproduction, fertility preservation, in vitro production of livestock, or animal breeding, comprising a method provided herein and warming the biological material and fertilizing and/or implanting the biological material; and a method for stem cell therapy comprising a method provided herein and further comprising warming the biological material and administering the biological material to a subject in need of stem cell therapy.

In some embodiments the technology provides a cryopreserved biological material, e.g., produced by a method, device, or system described herein, for use as a medicament, e.g., for stem cell therapy, regenerative medicine, or for assisted reproduction.

In some embodiments, the methods, systems, and cryopreserved biological materials described comprise use of a cryoprotectant agent such as glycerol, ethylene glycol, 1,2-propanediol, or DMSO; an impermeable solute; and/or a sugar, dextran, polyvinyl pyrrolidone, hydroxyethyl starch, sucrose, trehalose, raffinose, or stachyose. Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

FIG. 3A is a schematic diagram of a microfluidic device according to an embodiment of the technology. FIG. 3B shows zygotes held in the oocyte/zygote housing chamber prior to exposure to CPA and FIG. 3C shows zygotes held in the oocyte/zygote housing chamber after exposure for 690 seconds.

DETAILED DESCRIPTION

Provided herein is technology relating to cryopreservation and particularly, but not exclusively, to devices, systems, and methods for cryopreservation of biological materials such as oocytes and embryos. In this detailed description of the various embodiments, the section headings used herein are for organizational purposes only and are not to be construed as limiting the described subject matter in any way. For purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

By "cryoprotective agent", "cryoprotectant", or "CPA" is meant a compound used to slow or prevent ice nucleation, ice-crystal growth, ice formation, or any combination thereof. Cryoprotectants are generally agents with high water solubility and low toxicity. Included within this term are both permeating (e.g., glycerol, ethylene glycol, 1,2-propanediol, and DMSO) and non-permeating (impermeant) (e.g., sugars, dextran, polyvinyl pyrrolidone, and hydroxyethyl starch) cryoprotectants. Non-limiting examples of cryoprotectants that find use in the technology are various diols and triols (such as ethylene glycol, propylene glycol, glycerol, 1,2-propanediol, butanediol, and butanetriol), DMSO, sugars (e.g., sucrose, trehalose, raffinose, stachyose, and dextran), and various amides, such as formamide and acetamide. These compounds typically enter the cell by diffusing through the cell membrane and reach equilibrium in a relatively short time period. This diffusion into the cells can take from about 10 minutes to about 2 hours, after which the material is subjected to an appropriate freezing protocol.

By "vitrification" is meant a process of converting a material into a glass-like amorphous solid that is free of any crystalline structure. Vitreous solidification occurs at the glass transition temperature (which is lower than the melting temperature, $T_m$, due to supercooling).

By "cryopreservation solution" or "cryopreservation media" is meant any solution or media which is used to cool cells, either by slow-freezing or vitrification.

By "vitrification solution" or "vitrification media" is meant a solution or a media which is mixed with one or more cells prior to vitrification. Vitrification solutions can include, for example, PBS or any physiological solutions. A vitrification solution can be supplemented with one or more components including, but not limited to, serum, proteins, penicillin/streptomycin, lipids, salts, formamide, methoxylated compounds, polymers (e.g., polyvinyl pyrrolidone and polyvinyl alcohol), cryoprotectants, and/or sugars.

The terms "step-wise" and "multi-step" refer to the technique of changing the concentration of an intracellular cryoprotectant using discrete, stepped, increasing, or decreasing solute concentration differences in the diluent between steps to minimize potentially lethal osmotic changes in water diffusion across the cell membrane. During the freezing and thawing processes, cryopreserved cells undergo changes in intra- and extracellular solute concentrations as a result of changes in the amount of liquid water present. Additionally, water diffuses across the cell membrane more rapidly than cryoprotectants. "Continuous" techniques change the concentration of the cryoprotectant continuously such that discrete, stepped, abrupt changes in concentration are not apparent.

As used herein, "osmotic shock" or "osmotic stress" refers to a sudden change in the solute concentration around a cell (e.g., that changes the activity of water), causing a rapid change in the movement of water across its cell membrane and associated physical movements and stresses. Under conditions of high concentrations of either salts, substrates, or any solute in the supernatant, water is drawn out of the cells through osmosis. At low concentrations of solutes, water enters the cell in large amounts, causing it to swell and either burst or undergo apoptosis.

As used herein, a "heat pump" or "thermodynamic heat pump" is a device or system that transfers heat energy from a heat source to a heat sink against a temperature gradient. Heat pumps are designed to move thermal energy opposite the direction of spontaneous heat flow, e.g., away from a biological material to freeze it. A heat pump uses some amount of external high-grade energy to accomplish the desired transfer of thermal energy from heat source to heat sink.

Description

In contrast to previous osmotic stress studies based a minimum cell volume threshold to predict cryosurvivability, the technology provided herein acknowledges that cell health and future embryo developmental competence are also important for cryosurvivability. As such, embodiments of a microfluidic technology provide 1) improved fluid control and 2) the use of impermeable solutes to control osmotic stress resulting from shrinkage rate independent of osmotic stress arising from the amount of shrinkage that is reflected by the minimum cell volume. During the development of embodiments of the technology, experiments were conducted to vary the shrinkage rate in the microfluidic regime and a manual pipetting regime, while maintaining the minimum cell volume, to demonstrate the effects of shrinkage rate on sub-lethal damage to oocytes and/or zygotes. The data collected indicate that a more gradual shrinkage rate is beneficial, in particular by demonstrating a higher cytoplasmic lipid retention and better developmental competence as measured by the number of blastomeres per blastocyst. Although the disclosure herein refers to certain illustrated embodiments, it is to be understood that these embodiments are presented by way of example and not by way of limitation.

1. Automated Vitrification Based on Kedem-Katchalsky Equations

Cell membrane permeability and the volumetric change of a cell in response to a defined CPA concentration and temperature can be predicted (see, e.g., Kedem & Katchalsky (1958) *Biochim. Biophys. Acta* 27: 229-46). The Kedem-Katchalsky equations are generally used to describe substance transport across membranes (see, e.g., Kedem & Katchalsky (1958) *Biochim. Biophys. Acta* 27: 229-46; Katchalsky & Curran (1965) *Nonequilibrium Thermody-*

*namics in Biophysics*, pp. 113-32, Harvard University Press, Cambridge, Mass.). These equations have the following forms:

$$J_v = -L_p RT(\Delta C_i + \sigma \Delta C_s)$$ Equation 1

$$J_s = \omega RT \Delta C_s + J_v(1-\sigma)\overline{C}_s$$ Equation 2

In these equations, $J_v$ is the liquid volume flux through the cell membrane and $J_s$ is the solute flux through the cell membrane. The coefficients $L_p$, $\sigma$, and $\omega$ are related to the hydraulic conductivity (e.g., diffusive permeability) of the solute, the solute reflection or selectivity, and the solute permeability, respectively. R and T are the thermodynamic gas constant and temperature, respectively. $\overline{C}_s$ is the mean solute concentration, and $\Delta C_i$ and $\Delta C_s$ are the change in extracellular impermeable solute concentrations and change in extracellular permeable solute concentrations, respectively.

As applied to conventional vitrification technologies (e.g., methods comprising manual pipetting), the Kedem-Katchalsky equations (Equation 1 and Equation 2) generally did not include the effects of impermeable CPA in the vitrification solution and were given step-wise input functions for CPA concentrations. However, embodiments of the technology using microfluidics and a CPA as described herein expand the experimental possibilities to include continuous temporal gradients of CPA concentrations. In addition, models associated with the present technology account for the inclusion of impermeable CPA in the vitrification solution, which controls shrinkage rate independently of minimum cell volume. Experiments indicated that actual cell shrinkage agreed with that of mathematical modeling.

The models describe a shrinkage regime that has a constant cell shrinkage over time for the entire user-defined duration of the CPA exchange. Such a rate allows for the least amount of osmotic stress and the most gradual shrinkage rate while still providing an end result of a minimum cell volume associated with the presence of impermeable solutes. Experimental assessment of embodiments of the technology provided herein compares the performance of the embodiments relative to the idealized model, that is, data are collected to measure the deviation (% volume/time) of the shrinkage rate (% volume/time) as described in Equation 3:

$$\sigma = \sqrt{\frac{1}{n-1} \sum_{i=0}^{n} \left( f\left(\frac{i*t_f}{n}\right) - \frac{1}{t_f} \int_0^{t_f} f(t)dt \right)^2}$$ Equation 3 where $f(t)$ is the function of cell volume shrinkage rate over time (Equation 4), $t_f$ is the user-defined duration of CPA exchange, and n is the step number of computer analysis.

$$f(t) = \frac{dv}{dt}$$ Equation 4

According to the model, the ideal shrinkage regime provides the most gradual and constant shrinkage rate and thus the associated deviation $\sigma$ is 0. Using an n of 820,000, direct exposure of murine zygotes to an exposure regime known to cause catastrophic cell death (e.g., exposure to CPA for a $t_f$ of 720 seconds), $\sigma$ is 0.41% volume/second. The current conventional technology comprising manual pipetting brings the shrinkage regime closer to the ideal with a $\sigma$ of 0.19% volume/second. Finally, the technology provided herein related to the microfluidic device provides a shrinkage regime closer to the ideal with a $\sigma$ of 0.09% volume/second. In some embodiments, advanced syringe pumps capable of programmable flow profiles rather than linear gradients provide further improvements in the shrinkage regime, e.g., that decrease the % volume/second lower than approximately 0.09% to values closer to zero.

Based on these models and experiments that show the benefits of a lower osmotic stress by more gradual shrinkage rate during vitrification.

2. Microfluidic Device and Methods

Some embodiments provide a microfluidic device designed to minimize osmotic stress by Kedem-Katchalsky equations. In some embodiments, microfluidic devices were made using conventional photolithography and soft lithography, e.g., using a soft polymer (e.g., polydimethylsiloxane (PDMS)), a printed photomask, and a collimated UV light aligner (see, e.g., Quake et al (2000) *Science* 290: 1536-40; Melin et al (2007) *Annu Rev Biophys Biomol Struct* 36:213-31). Methods for fabricating microfluidic devices (including suitable materials, dimensions, design principles, and operation) are provided, for example, in U.S. patent application Ser. Nos. 11/685,654; 11/056,451; 09/826,583; 09/724,784 and 09/605,520, which are incorporated herein by reference in their entireties.

The technology is not limited by the materials that are used to construct the microfluidic device. Indeed, the microfluidic device can be made of any material, e.g., materials having desirable thermal conducting properties (e.g., greater than 10 $Wm^{-1}K^{-1}$) and/or having translucency such as quartz, CVD diamond, and diamond-like materials (e.g., graphene). In some embodiments, a microfluidic device has sufficiently thin walls to provide optical translucency and a high thermal conductance. In some embodiments, materials are thin enough such that materials of lower thermal conductance are used. For example, conventional cryotops and cryoloops comprise plastic structures approximately 100 μm thick.

In some embodiments, the device comprises two layers: 1) a microfluidic channel layer that houses the oocytes and/or embryos and delivers the CPA solutions; and 2) a holding pipette layer that provides a vacuum to hold the oocytes and/or embryos stationary under the conditions of constant volumetric flow and changing viscosity and fluid density associated with the changing CPA concentration.

Figure 3:
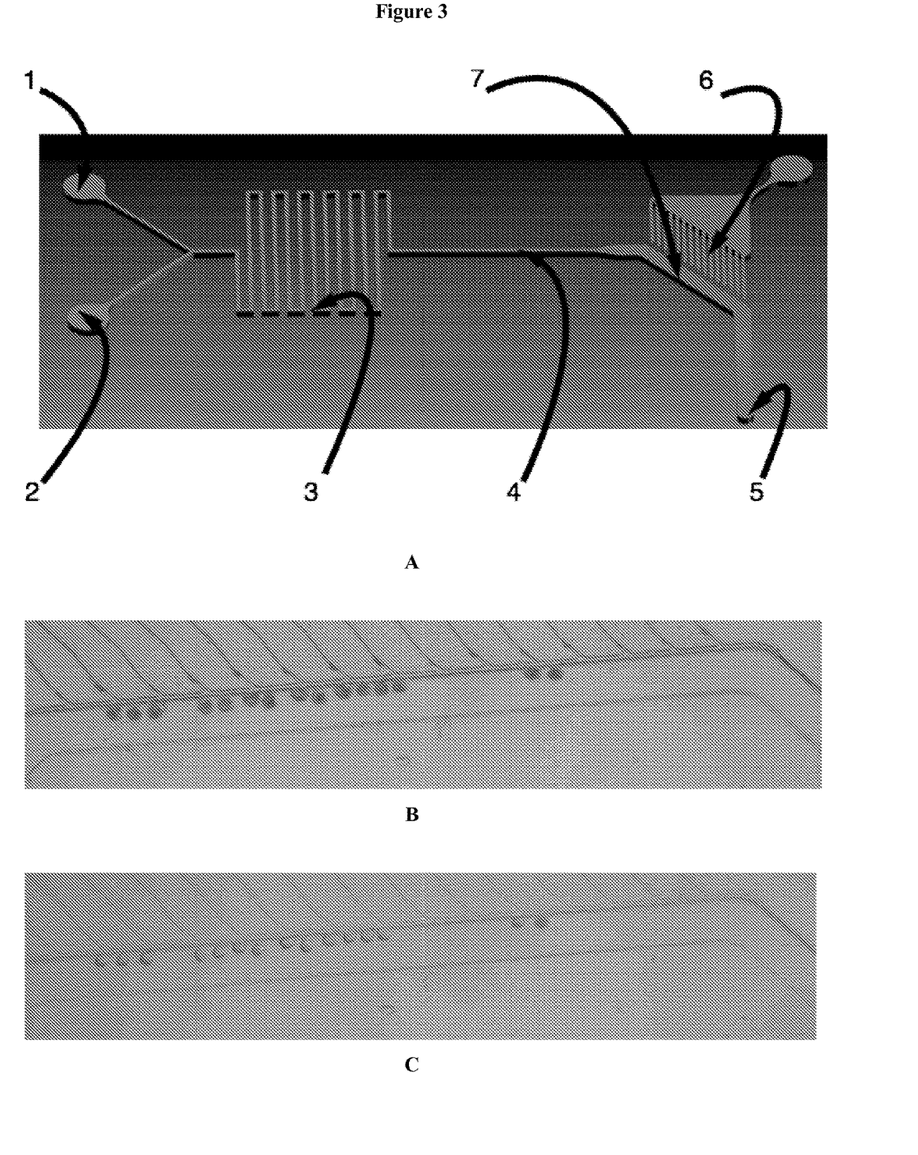
FIG. 3 shows a schematic and images of an embodiment of the microfluidic device.

In an exemplary embodiment (FIG. 3A), microfluidic devices comprise an input for culture medium 1 (e.g., in operable fluid communication with a syringe pump providing culture medium), an input for a solution comprising a CPA 2 (e.g., in operable communication with a syringe pump providing a solution comprising CPA), a serpentine mixing channel 3 for fluid mixing (e.g., to mix the culture medium and the solution comprising the CPA to provide a continuous perfusion of vitrification solution comprising a CPA concentration that changes as a function of time, e.g., to provide a gradient of CPA to the embryos and/or zygotes), a delivery channel 4 for providing the vitrification solution (e.g., a continuous perfusion of CPA that changes as a function of time, e.g., to provide a gradient of CPA to the embryos and/or zygotes) to the oocytes and/or embryos, an oocyte/embryo housing chamber 7, and a set of height-differential vacuum powered holding channels 6 that maintain the oocytes and/or zygotes in the oocyte/zygote housing chamber 7 (FIG. 3A, FIG. 3B, FIG. 3C). In some embodiments, the device comprises a port 5 (e.g., having a diameter of approximately 100 to 300 μm, e.g., approximately 200 μm, e.g., as created by a 200 μm microdrill bit) for the loading and withdrawal of oocytes and/or embryos from the device. The port and vacuum control provide an efficient method of retrieval of oocytes and/or embryos. In some embodiments, the device does not have edges or corners on which oocytes and/or embryos could become stuck within the device. In some embodiments, the device provides for the real-time visual monitoring of the cryopreservation, which is a feature that was previously not attainable in manual pipetting protocols.

According to embodiments of the technology, a continuous temporal gradient of CPA concentrations (e.g., a continuously changing mixture of CPA and culture medium) is produced by two programmable syringe pumps in operable communication with the microfluidic device as controlled by an automated CPA mixing and exposure protocol. In some embodiments, one programmable syringe pump provides an increasing (e.g., linearly increasing) flow rate of CPA (e.g., vitrification solution) and one programmable syringe pump provides a decreasing (e.g., a linearly decreasing) flow rate of culture medium that, when mixed in the device, provide a linearly increasing concentration of CPA to the device. Other modes of operation that provide a CPA gradient are contemplated by the technology (e.g., other non-linear flow rates and/or non-linear gradients).

In some embodiments of methods associated with the technology, methods comprise loading oocytes and/or zygotes. In some embodiments, loading comprises activating a suction channel. In some embodiments, the suction channel is powered by a negative height differential in the absence of syringe flow through the loading/withdrawal port. In some embodiments, pumping (e.g., synchronized pumping) by the two programmable syringe pumps provides a continuous temporal CPA exchange. In some embodiments, one syringe comprises a solution comprising pure culture media and one syringe comprises a solution comprising vitrification solution. In some embodiments, one syringe provides a concentration of culture medium that decreases as a function of time (e.g., decreases linearly as a function of time) and one syringe provides a concentration of vitrification solution that increases as a function of time (e.g., increases linearly as a function of time). In some embodiments, the outputs of the two syringes are mixed, e.g., using a serpentine mixing channel, to produce a constant flow of media comprising a linearly increasing CPA concentration over time.

In some embodiments, the media is passed through the exposure chamber where one or more oocytes and/or zygotes (e.g., 1, 2, 3, 4, 5, 6, 7, 8, 9, 10, 11, 12, 13, 14, 15, 16, 17, 18, 19, 20, 30, 40, 50, 60, 70, 80, 90, 100, or more than 100) is/are immobilized by the holding channels via the continued activation of the suction channels. In some embodiments, the methods comprise releasing the cells out of the device through the loading/withdrawal port, e.g., by terminating the suction in the presence of syringe flow. Experiments conducted during the development of embodiments of the technology indicated the reliability and versatility of the automated microfluidic device by vitrifying approximately 500 murine or bovine oocytes and zygotes with 100% recovery (n=474) and the capability of vitrifying up to 15 oocytes and/or zygotes simultaneously in an exemplary embodiment of the device.

3. CPA Solutions

Vitrification is the solidification of a sample while maintaining the absence of both intracellular and extracellular ice. This glassy state can be induced in most liquids and the use of cryoprotective agents (CPA) further decreases the deleterious effects of this cooling. Among the most commonly used CPA are dimethyl sulfoxide (DMSO), glycerol, ethylene glycol, and 1,2-propanediol.

Impermeable solutes such as glucose, fructose, sorbitol, sucrose, trehalose, and raffinose contribute positively to the vitrification properties of solutions used to preserve biological materials (e.g., oocytes and embryos) (see, e.g., Kuleshova et al., Cryobiology 1999 38:119-130). Nevertheless, the components and concentrations of components in vitrification solutions and the exposure protocols vary from application to application, e.g., for different cell types and/or species.

Embodiments comprise use of a vitrification solution comprising at least one, two, three, or more cryoprotective agents. The CPA includes, but is not limited to, sugar (e.g., sucrose, trehalose, raffinose, stachyose, and dextran), glycerol, polypropylene glycol, ethylene glycol, 1,2-propanediol, and DMSO. The CPA or combination of CPAs is desirably present at a concentration less than or equal to 4 M, 3 M, 2.5 M, 2 M, 1 M, 0.5 M, 0.3 M, or less. The combination of CPAs can include any of these concentrations of each CPA. For example, one CPA can be present at a concentration of 2 M, while the other is present at 0.5 M or 0.3 M. Examples of combinations of CPAs include 1,2-propanediol and a sugar or ethylene glycol and a sugar. In some embodiments, the vitrification solution also includes at least one nanoparticle or microparticle. Exemplary nanoparticles or microparticles include a carbon or noble metal (e.g., gold, silver, titanium, palladium, platinum, and copper). In some embodiments, the vitrification solution also includes at least one polymer or peptide (e.g., an ice blocker) that inhibits ice nucleation and growth in the vitrification solution. Non-limiting examples of the polymer or peptide include polyvinyl alcohol, polyglycerol, and antifreeze proteins. For example, exemplary embodiments use a solution of 15% ethylene glycol, 15% DMSO, 0.5 M sucrose, and 12% serum substitute supplement (SSS). In other embodiments, the technology uses a solution comprising 15% ethylene glycol, 15% DMSO, 0.5 M sucrose, and 20% SSS. Additional examples are known in the art.

4. Samples

The present technology can be used for the cryopreservation of any type and any species of one or more mammalian cells. For example, in some embodiments the technology is used to cryopreserve oocytes, zygotes, or sperm in assisted reproductive technology or for patients undergoing chemotherapy or radiation therapy. The technology is used in some embodiments for the cryopreservation of stem cells or stem cell products, such as embryonic stem cells, embryoid bodies, organoids, or other cells, which can then be used as the basis of stem cell-based therapies, cell transplantation, tissue engineering, and regenerative medicine. The technology finds use in some embodiments to cryopreserve oocytes, zygotes, or sperm from an animal that is rare or at risk of becoming extinct for future use in assisted reproductive technologies for the preservation of the species. The technology finds use for animal husbandry purposes (e.g., the breeding and raising of animals), for example, for the cryopreservation of embryonic stem cells, gametocytes, oocytes, zygotes, or sperm from animals such as cows, pigs, and sheep.

Cell types that are cryopreserved according to some embodiments of the technology include, for example, differentiated cells, such as epithelial cells, cardiomyocytes, neural cells, epidermal cells, keratinocytes, hematopoietic cells, melanocytes, chondrocytes, B-cells, T-cells, erythrocytes, macrophages, monocytes, fibroblasts, or muscle cells; and undifferentiated cells, such as embryonic, mesenchymal, or adult stem cells. Additional cell types that are cryopreserved using the technology include gametocytes, oocytes, sperm, zygotes, and embryos. The cells can be haploid (DNA content of n; where "n" is the number of chromosomes found in the normal haploid chromosomes set of a mammal of a particular genus or species), diploid (2n), or tetraploid (4n). Other cells include those from the bladder, brain, esophagus, fallopian tube, heart, intestines, gallbladder, kidney, liver, lung, ovaries, pancreas, prostate, spinal cord, spleen, stomach, testes, thymus, thyroid, trachea, ureter, urethra, or uterus.

In some embodiments, the cells are from a human or non-human mammal, for example Cercopithecoidea family, Hominoidea superfamily, *Canis familiaris*, *Felis catus*, *Cricetidae* spp., *Equus* spp. (e.g., *Equus caballus*, *Equus assinus*), Equidae family, *Bos taurus*, *Bos indicus*, Bovidae family, Camelidae family, *Bubalus bubalis*, *Capra aegagrus hircus*, Cervidae family, Cervinae family, *Ovis aries*, *Ovis canadensis*, *Capra hircus*, *Sus scrofa domestica*, *Mesocricetus* spp., *Mustela vison*, *Cavia porcellus*, *Meriones unguiculatus*, *Chinchilla laniger*, *Rattus norvegicus*, *Rattus* spp., *Mus musculus*, Leporidae family, *Oryctolagus cuniculus*, *Kobus* spp., *Gallus* spp., *Meleagria gallopavo*, *Anatidae* spp., *Mustela putorius*, *Columba domestica*, *Columba livia*, *Numida meleagris*, *Ornithorhynchus anatinus*, *Pavo cristatus*, *Bison* spp., *Struthio* spp., *Lama glama*, *Rhea* spp., *Dromiceius* spp., *Lama pacos*, *Rangifer tarandus*, *Bos grunniens*, *Camelus bactrianus*, *Camelus dromedarius*), and any endangered or threatened species (e.g., those species identified by the U.S. Fish and Wildlife Service (USFWS) Threatened and Endangered Species System (TESS)).

In some embodiments, the cells are prepared for cryopreservation using techniques known in the art and described herein. Generally, the mammalian cells are obtained using art-known techniques and maintained in media appropriate for the cell type. The cells are then mixed with a vitrification solution. The concentration of the cells in the vitrification solution varies depending on the cell type. For example, for oocytes, the concentration of cells can be low, for example, as low as <1 cell/ml, while for stem cells, the cell concentration can be higher. The exact concentration can be determined by the skilled artisan for the particular cell type.

The vitrification solution can comprise any physiologic solution such as phosphate buffered saline (PBS), FHM (a flush hold Hepes-buffered medium from Specialty Media, Lavallette, N.J.), or a cell media, for example, a stem cell culture medium that includes Knockout DMEM+15% Knockout Serum Replacement (Invitrogen, Carlsbad, Calif.) containing 1000 U/ml Leukemia Inhibitory Factor (Chemicon, Temecula, Calif.). The vitrification solution is desirably supplemented with one or more components including, but not limited to, serum, proteins, penicillin/streptomycin, lipids, salts, formamide, methoxylated compounds, polymers (e.g., polyvinyl pyrrolidone and polyvinyl alcohol), cryoprotectants, and/or sugars.

Example 1

Materials and Methods

Kedem-Katchalsky Modeling. The device was designed to minimize osmotic stress by Kedem-Katchalsky equations using MatLAB (MathWorks, Natick, Mass.). The osmolarity contributions of each CPA component in the VS is assumed to be additive. $L_p$ is $8.94*10^{-7}$ cm/sec/atm, $\omega_{DMSO}$ is $2.54*10^{-5}$ cm/sec, $\omega_{EG}$ is $1.0*10^{-5}$ cm/sec $t_f$ is the user-defined duration of CPA exchange, and n is the step number of computer analysis. The solvent/solute interaction, σ did not have a dramatic effect on model.

Device design and fabrication. The microfluidic device was designed to minimize osmotic stress as predicted by Kedem-Katchalsky equations. Microfluidic devices were made using conventional photolithography and soft lithography using polydimethylsiloxane (PDMS), a photomask printed by, and a collimated UV light aligner. The device comprises 1) a microfluidic channel layer that houses the oocytes and/or embryos and that delivers the CPA solutions; and 2) a holding pipette layer that provides the vacuum to hold the oocytes and/or embryos stationary under the constant volumetric flow rate but changing CPA concentrations and associated viscosity and fluid density.

The device was designed to comprise a serpentine mixing channel for fluid mixing, an oocyte/embryo housing chamber. A set of height-differential vacuum powered holding channels were reverse engineered from glass holding pipettes commonly used in reproductive science laboratories. The loading and withdrawal of oocytes and/or embryos from the device was through a port drilled by a 200 µm microdrill bit (Kyocera) into a glass slide (Fisher) on which the PDMS is bonded to provide laminar flow in and out of the device). This combined with control of vacuum created an effective method of retrieval with no edges or corners for oocytes/zygotes to be trapped within the device. The device was characterized for efficient mixing and linear CPA exposure using fluorescence quenching and fluorescence microscopy (data not shown) and operated at 700 µL/hr total flow rate from a synchronized culture media syringe pump and VS syringe pump.

Oocyte/zygote loading, trapping, and withdrawal. Loading of oocyte/zygotes through the loading/withdrawal port is achieved by activation of the suction channel powered by a negative height differential (~10 cm) in the absence of syringe pump flow. The activation and deactivation of the suction channel is operated by a 3-way valve at the end of the height differential. The exposure chamber contains 15 holding microchannels where up to 15 oocytes/zygotes are immobilized via the continued activation of the suction port. The cells are released out of the device through the loading/withdrawal port by the termination of suction port in the presence of syringe pump flow.

Automated and Manual Vitrification.

Automated vitrification was achieved by two programmable syringe pumps (Chemyx, Stafford, Tex.) capable of providing linear gradients. The vitrification solution syringe pump was programmed to provide a linearly increasing flow rate from 0 to 700 µL/hr in 10 minutes. The culture media syringe pump was programmed to provide a linearly decreasing flow rate from 700 to 0 µL/hr in 10 minutes. After mixture by serpentine channel, the solution of constantly flow rate ~700 µL/hr but changing CPA concentrations from culture media to vitrification solution conditions is delivered to the exposure chamber to exposure cells. During operation, the spent fluid escapes via the loading/withdrawal port as well as the suction port. The media that escapes from the loading/withdrawal port is discarded.

Manual vitrification for MII oocytes and zygotes was performed as previously described (Smith and Fioravanti, 2006) with slight modification. Briefly, mouse or bovine MII oocytes were transferred to 20 µl of washing solution drop for 1 minute, then merged with two 20-µl equilibration solution drops sequentially for 2 minutes at each merging; finally, the oocytes were transferred to equilibration solution for 2 to 3 minutes. After equilibration, oocytes were transferred through three 20-µl vitrification solution drops for 5 seconds, 5 seconds, and 10 seconds, and then maintained in the fourth drop of vitrification solution until freezing. HSV straws (MediCult) were used for loading oocytes and the loaded straws were plunged into liquid nitrogen within a 90-second interval. Vitrification procedures for mouse zygotes were similar as those for oocytes, except for a longer incubation (8 minutes) in equilibration solution.

Oocyte and Zygote Harvest.

All procedures described within were reviewed and approved by The University Committee on Use and Care of Animals at the University of Michigan and were performed in accordance with the Guiding Principles for the Care and Use of Laboratory Animals.

Bovine ovaries were obtained from a local abattoir at random stages of the estrous cycle or pregnancy and transported to the laboratory in warmed PBS containing antibiotics. Cumulus-oocyte complexes were aspirated from follicles of 2-6 mm diameter and matured for 24 h in M199 medium (Sigma-Aldrich, St. Louis, Mo.) at 39° C. in 5% $CO_2$, 5% $O_2$, and 90% $N_2$. Mature oocytes were then denuded of cumulus cells before use.

Meiotically competent germinal vesicle intact (GVI) oocytes were collected from antral follicles of 21-23d old CF-1 female mice (Harlan, Indianapolis, Ind.) ovaries 44-46 h after 5 IU equine chorionic gonadotropin (eCG, Sigma-Aldrich, St. Louis, Mo.) stimulation. Denuded GVI oocytes were triple washed in human tubal fluid-HEPES (HTFH, Irvine Scientific, Santa Ana, Calif.)/0.3% BSA and cultured in HTF/0.3% BSA at 37° C. in 5% $CO_2$ incubator for 18 h to obtain MII oocytes.

Female B6C3F1 mice at 6 to 8 weeks old were injected with 5 IU equine chorionic gonadotropin (eCG, Sigma-Aldrich, St. Louis, Mo.) for zygote collection. Forty-eight hours later, mice were injected with 5 IU human chronically gonadotropin (hCG, Sigma-Aldrich, St. Louis, Mo.). Upon hCG injection, female mice were placed with mature B6C3F1 males of known fertility until sacrificed 18 hours later. Zygotes were released from the ampulla, denuded in human tubal fluid-HEPES (HTFH, Irvine Scientific, Santa Ana, Calif.)/0.1% Hyaluronidase, triple washed in HTFH/0.3% BSA and placed in pre-equilibrated potassium simplex optimized medium (KSOM)+amino acids (AA) (Millipore, Billerica, Mass.) at 37° C. in 5% $CO_2$ incubator until use.

Microscopy, Roughness Index, and Sphericity.

Zygotes were analyzed at 400× magnification for conventional microscopy. The roughness index was quantified as standard deviation of the grey values within the region of interest (ROI). The ROI was defined as the middle 50% of cell surface so that edge effects are nullified. The zygotes were oriented such that the polar bodies do not visually obstruct the center of the zygote. Zygotes exposed to CPA by automated or manual pipetting protocols were stained by Hoechst 33342 at 5 µg/ml for 10 min but unwashed to retain cytoplasmic staining. The Hoechst stained zygotes were analyzed using confocal microscopy. The volume and surface area were then quantified using ImageJ to calculate sphericity.

Warming and Embryo Culture, and Developmental Competence Analysis.

Independent of CPA exposure/vitrification treatments, murine oocyte and zygote warmings were performed manually by fully trained individuals using a previously described technique (Smith and Fioravanti 2007). Murine zygotes, either no CPA exposure or vitrification (NCEV) or vitrified and warmed were transferred to 50 µl pre-equilibrated KSOM+AA microdrops under oil and cultured at 37° C. in 5% $CO_2$, 5% $O_2$, 90% $N_2$ gaseous conditions. Embryo morphologies in each experimental group were assessed at 96 hours of culture for blastocyst development using an inverted microscope (200×; Leica DM2RB, Wetzlar, Germany).

Cytoplasmic Lipid Content.

Bovine oocytes in control, automated, and manually vitrified groups were fixed on poly-L-lysine-coated coverslips by incubation in 2% paraformaldehyde overnight. Fixed oocyte samples were triple washed with 1× phosphate-buffered saline (PBS) the next day, stained with 100 nM Nile Red (Sigma) for 20 minutes at room temperature, then washed one time with PBS and stained with Hoechst 33342 (5 µg/ml) for 10 minutes. After Hoechst staining, oocyte samples were triple washed with 1×PBS and mounted using 90% glycerol comprising an anti-fading reagent. Lipid contents in bovine oocytes were visualized under confocal microscope. Statistical comparisons of samples were by Anova followed by student's t-test.

Cytoplasmic Leakage.

Murine zygotes were exposed to CPA by automated-microfluidics and manual-pipetting using vitrification solutions and equilibration solutions supplemented with 100 mg/mL 4 KDa FITC-dextran (Sigma-Aldrich, St. Louis, Mo.). The fluorescence intensity of each zygote was recorded by fluorescence microscopy and normalized to NCEV murine zygotes treated in culture medium with FITC-dextran supplement for 12 minutes. After CPA exposure, the zygotes were carefully washed in regular vitrification solution twice to eliminate extracellular FITC-dextran. NCEV zygotes were also carefully washed in regular culture medium in the same manner. Special care was taken during sample preparation and image capture to have identical sample volume, excitation wavelength, excitation energy, and exposure time.

Developmental Competence Analysis.

To count blastomere numbers, blastocysts from control, automated, and manually vitrified groups were fixed on poly-L-lysine-coated coverslips by incubating in 2% paraformaldehyde overnight. Fixed blastocyst samples were triple washed in PBS the next day, stained with Hoechst 33342 (5 µg/ml) for 10 minutes, triple washed with PBS, and then mounted using 90% glycerol comprising an anti-fading reagent. Blastomere numbers were counted under a fluorescent microscope (400× power) in blind fashion. Statistical comparisons of samples were by Anova followed by Student T-test.

Statistical Analysis.

All statistical analyses were parametric and conducted first using ANOVA followed by pair-wise comparisons using unpaired student's t-test. Statistical significance was determined at the 95% confidence interval and performed using R (Vienna University of Economics and Business, Vienna, Austria). Statistical significance of $p<0.05$ is graphically represented by different smaller case letters.

Results

Modelling Cell Shrinkage with the Kedem-Katchalsky Equations.

A cell's volumetric change upon exposure to CPA can be accurately modeled (Kedem and Katchalsky, *Biochim Biophys Acta* 1958; 27:229-246; Pfaff, *Mol Hum Reprod* 1998; 4:51-59; Paynter et al., *Cryobiology* 1999; 39:169-176). Kedem-Katchalsky equations (Eq 1-2) typically use stepwise input functions of CPA concentrations, as this is the experimental limitation of manual pipetting. Where $J_v$ is the liquid volume flux through the cell membrane and $J_s$ is the solute flux through the cell membrane. The coefficients $L_p$, σ, and ω are related to the hydraulic conductivity, the solvent/solute interaction factor, and the solute permeability. R and T are the gas constant and temperature. $\overline{C}_s$ is the mean solute concentration, and $\Delta C_i$ and $\Delta C_s$ are the change in impermeable solute concentrations and change in permeable solute concentrations, respectively.

$$J_v = -L_p RT(\Delta C_i + \sigma \Delta C_s) \qquad \text{Eq 1:}$$

$$J_s = \omega RT \Delta C_s + J_v(1-\sigma)\overline{C}_s \qquad \text{Eq 2:}$$

Figure 1:
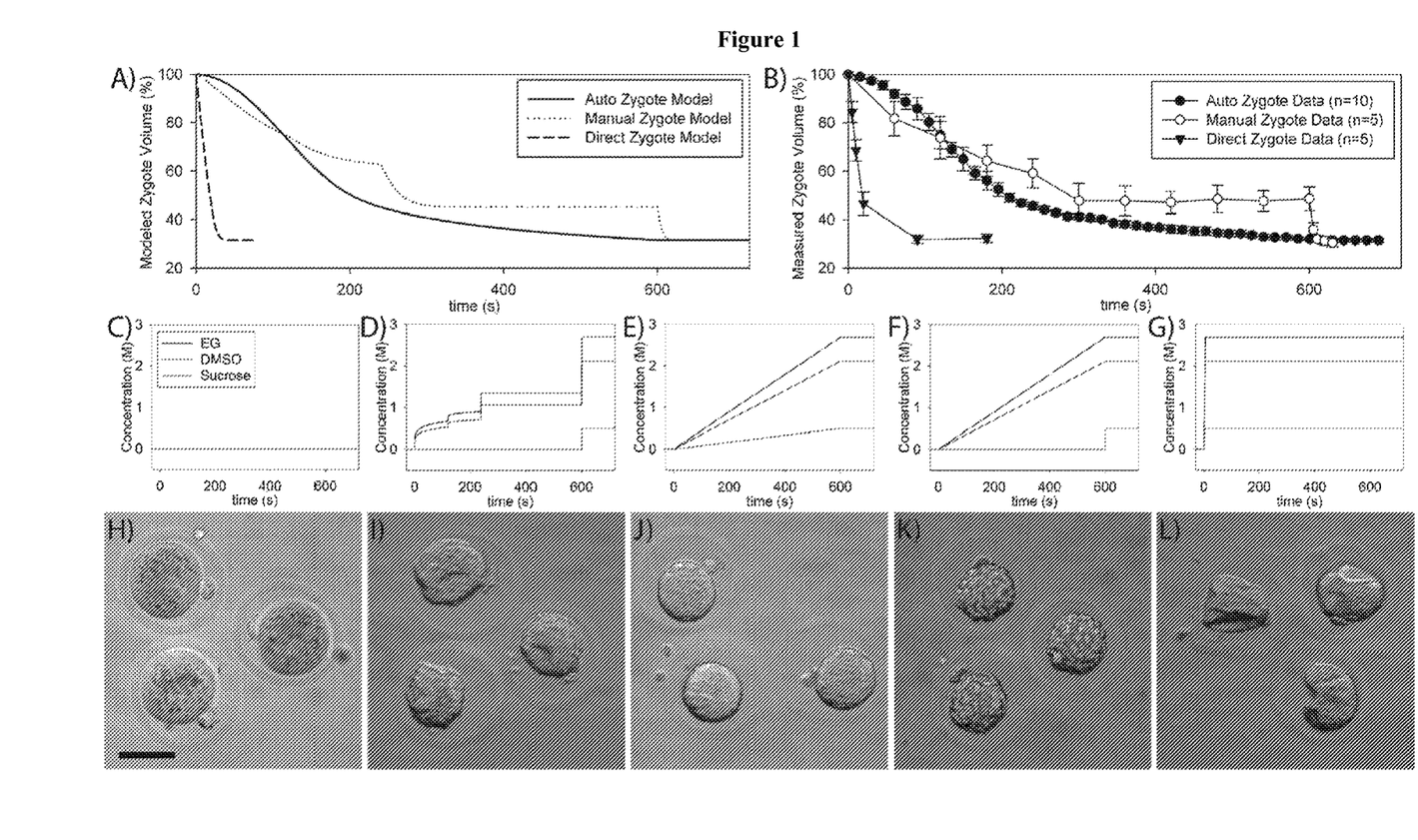
FIG. 1 shows A) Kedem-Katchalsky model of zygote shrinkage during cryoprotectant agent (CPA) exchange protocols. B) Experimental observation of zygote volumes matched that of predictive models. CPA exchange profiles and representative morphology for: C,H) No CPA exposure or vitrification (NCEV), D,I) Commonly used manual pipetting protocols, E,J) Automated microfluidic protocol with gradual addition of all CPA components with smoother and rounder morphology than alternative CPA exposure protocols, F,K) Gradual exposure of permeable CPA components but abrupt exposure to the impermeable component sucrose, and G,L) Direct and sudden exposure from culture media to VS.

However with the use of microfluidics, the experimental possibilities include continuous temporal gradients of CPA concentrations using ethylene glycol (EG), dimethyl sulfoxide (DMSO), and sucrose. Although a related mathematical analysis was performed by Heo and colleagues, they did not consider the inclusion of impermeable CPAs, such as sucrose, in the vitrification solution (VS) as is highly recommended for practical cryopreservation (Kuleshova et al., *Cryobiology* 1999; 38:119-130) and useful to control shrinkage rate independently of minimum cell volume (FIG. 1A).

Direct exposure to VS gives the fastest maximal shrinkage rate of 7.51% volume/sec and the highest osmotic shock. The current clinically-used manual-pipetting protocol causes a shrinkage pattern that is at times shrinking quickly, while at other times static. The sudden introductions of CPA from manual-pipetting also produced fast shrinkage rates with a maximum of 4.13% volume/sec. Automated microfluidic CPA exchange (auto-microfluidics) which we hypothesize to have the lowest osmotic stress prevents instances of quick cell shrinkage by eliminating sudden changes in osmolality, producing maximum shrinkage rates of only 0.35% volume/sec. If assumed spherical, the maximal surface area strain rate of the cell membrane for auto-microfluidics is 13.8 times and 22.5 times less than the maximal strain rate of manual-pipetting and direct exposure respectively. The cell membrane buckling observed under conditions of fast shrinkage rates is consistent with the known viscoelastic nature of the cell membrane-cytoskeleton complex (Ragoonanan et al., *Cryobiology* 2010; 61:335-344; Fu and Zhang, *Arch Appl Mech* 2012; 82:69-77).

Zygote Vitrification Affecting Morphology and Cryosurvival.

Murine zygotes with no CPA exposure or vitrification (NCEV), alternatively referred to as fresh or non-treated zygotes, (FIG. 1C,H) were compared to those subjected to CPA exposure regimes (FIG. 1D-G). The direct exposure (FIG. 1G,L) represents transfer of zygotes directly from culture media to VS, a protocol known to be detrimental to cryosurvival (59.6±3.2%, n=40). Experimental cell shrinkage profiles (FIG. 1B) agree well with models (FIG. 1A). Despite differences in cell shrinkage profile, zygotes from manual-pipetting (FIG. 1D,I) and auto-microfluidic (FIG. 1E,J) CPA exposure both exhibit high cryosurvival (100±0%, n=200 and 100±0%, n=224, respectively) after vitrification and warming.

Despite shrinkage to roughly the same final cell volume, there was significant differences in cell morphology depending on the CPA exchange protocol. High magnification images reveal a significantly smoother and more spherical morphology when using a more uniform and gradual shrinkage rate enabled by microfluidic CPA exposure (FIG. 1I,J). Confocal images further highlight morphological differences between manual-pipetting and auto-microfluidic CPA exchange. Additional morphology-focused CPA exchange studies demonstrate the importance of applying sucrose, the impermeable component of the vitrification solution gradually (FIG. 1E,J) for a smooth cell surface in comparison to abrupt sucrose addition (FIG. 1F,K). Finally, direct VS exposures (FIG. 1G,L) demonstrated the importance of avoiding abrupt permeable and impermeable CPA exposures to alleviate the large crater-like deformations on the cell membrane that are also visible in manual-pipetting protocols (FIG. 1I), where cell water volume may escape unevenly due to high gradient of CPA concentrations preferentially on one side of the cell.

Figure 2:
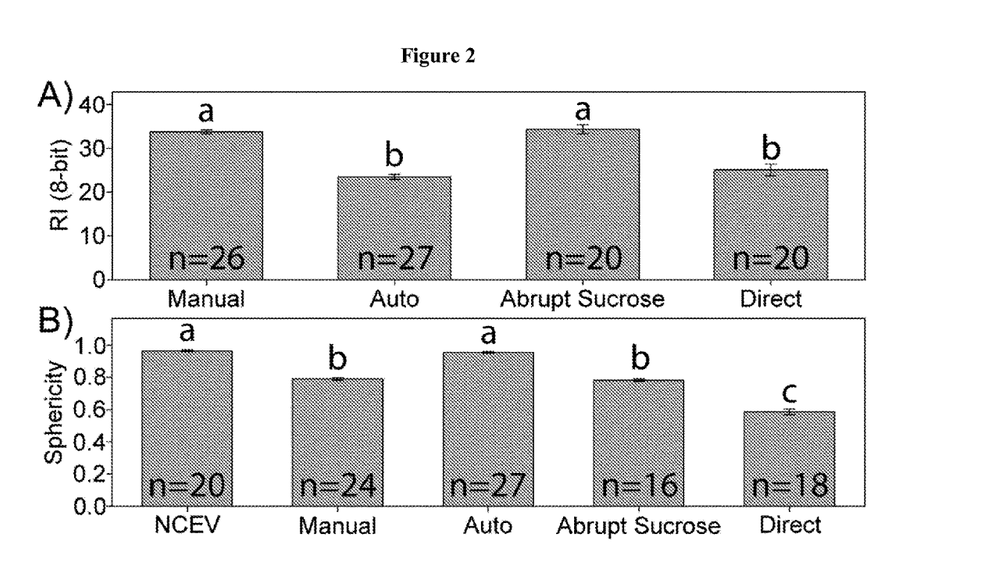
FIG. 2 shows that A) Murine zygotes subjected to automated microfluidic CPA (Auto) exposure had significantly ($p<0.001$) smoother cell surface than manual pipetting-based CPA (Manual) exposure. B) Confocal microscopy reveals that murine zygotes subjected to Auto exposure have significantly higher spherical morphology ($p<0.001$) than Manual.

Zygote surface smoothness was quantified while in vitrification solution under microscopy. Rough surfaces cast dark and light areas on the cell surface. The roughness index (RI) is quantified as the standard deviation of the grey value of the cell. Confocal microscopy was also used to measure cell surface area and volume to calculate sphericity. Zygotes exposed to automated microfluidic CPA exposure (FIG. 1E,J; RI=23.50±0.69, n=27; sphericity=0.956±0.004, n=27) are significantly (p<0.001) smoother and more spherical morphology than its manual pipetting counterpart (FIG. 1D,I; RI=33.72±0.47, n=26; sphericity=0.790±0.008, n=24) (FIG. 2A,B). Gradual EG and DMSO but abrupt sucrose exposure also have rough surfaces and sphericity that is statistically comparable to manual pipetting which also consists of abrupt exposure to sucrose (RI=34.32±1.02, n=20; sphericity=0.783±0.008, n=16). Direct exposure had smooth surfaces despite an abrupt exposure to all CPAs: EG, DMSO and sucrose (RI=25.08±1.33, n=20), but develop large concave morphology that resulted in the lowest sphericity (sphericity=0.586±0.017, n=18). NCEV zygotes had visual occlusions that cast dark regions in microscopy due to significant differences in refractive indexes in its cytoplasmic content. The lack of EG and DMSO, which homogenizes refractive indexes of cytoplasmic content, prevented the direct comparison of NCEV zygotes to other experimental groups, although NCEV zygotes clearly have a smooth surface as observed visually by the human eye and its smooth surface allowed it to have high sphericity (sphericity=0.965±0.006, n=20).

Microfluidic Device Design.

Continuous temporal gradient of CPA concentrations is realized by two synchronized programmable syringe pumps connected to the inlets of the microfluidic device with geometry-mediated CPA mixing and exposure embedded into device design (FIG. 3A). Immobilized by holding microchannels within the exposure chamber, the microfluidic device allows for real-time monitoring by microscopy (FIG. 3B). The loading/withdrawal port is a 200 μm microdrilled hole within the glass substrate that is aligned to the end of the PDMS channel. It loads cells when the suction is activated in the absence of syringe flow and functions as a cell withdrawal port when the suction is deactivated in the presence of syringe flow. The suction microchannels (20 μm by 20 μm) are powered by a negative height differential and is activated/deactivated by a 3-way valve. Abnormal deformation in the zona pellucida was observed at ~18 cm $H_2O$. As such, a height differential of ~10 cm was used and the flow velocity was adjusted such that the cells would remain trapped during syringe flow. The size of the cell loading/withdrawal port allow for laminar flow at the outlet that prevented cell entrapment within the device. The reliability and versatility of the automated microfluidic device was demonstrated by vitrifying 462 murine or bovine oocytes and zygotes with 100% recovery as well as the capability of vitrifying up to 15 oocytes/zygotes simultaneously.

Increased Bovine Cytoplasmic Lipid Retention.

Figure 4:
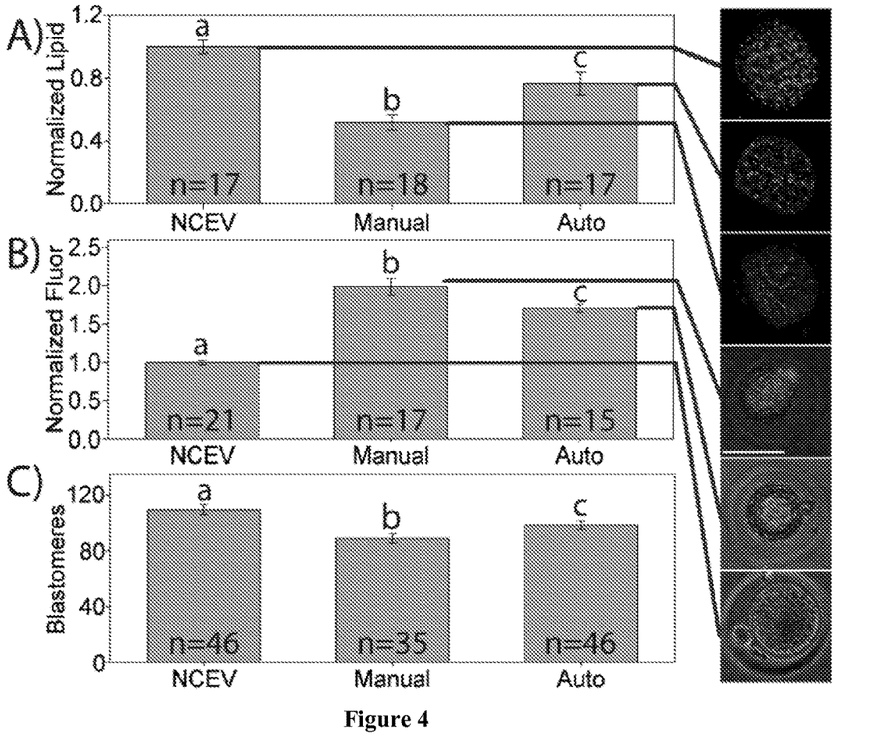
FIG. 4 shows that A) Vitrification causes a loss of cytoplasmic lipid for bovine oocytes. However the use of automated-microfluidic (Auto) CPA exposure increases cytoplasmic lipid retention compared to manual-pipetting (Manual) CPA exposure ($p<0.01$). B) A lower shrinkage rate from Auto causes a significantly lower amount of cytoplasmic leakage from membrane damage than Manual as quantified by influx of FITC-dextran during CPA exposure ($p<0.05$). C) Vitrification-derived sub-lethal damage decreases developmental competence after 96 hours of embryo culture of murine zygotes.

Bovine oocytes were used due to their more similar size and developmental characteristics to human oocytes (Chian et al., *J Reprod Dev* 2004; 50:685-696). Bovine oocytes from the manual-pipetting and auto-microfluidic methods were studied to demonstrate the biological advantages of lowering shrinkage rate. Confocal images of bovine oocytes with Nile Red staining were normalized to NCEV oocytes at 100±0.04% (n=17) lipid content to characterize post-warming cytoplasmic lipid retention. Vitrified bovine oocytes using manual-pipetting CPA exposure have significantly lower cytoplasmic lipid retention 51.8±0.05% (n=18) than bovine oocytes vitrified using auto-microfluidic CPA exposure 76.6±0.07% (n=17; $p<0.01$; FIG. 4A).

Decreased Membrane Perforations and Cytoplasmic Leakage.

Murine zygotes were exposed to CPA supplemented with 4 KDa FITC-dextran, an impermeable and fluorescent solute, by auto-microfluidic or manual-pipetting treatment groups. Entrance of FITC-dextran into cells is used as an indicator of membrane damage (Miyake et al., *J Cell Sci* 2001; 114:3487-3494). The auto-microfluidics protocol that realizes slower zygote shrinkage rate had significantly lower fluorescent signal (1.71±0.05; n=15) compared to cells from the manual-pipetting protocol that induces higher shrinkage rates (1.99±0.11; n=17; $p<0.05$). The lower FITC-dextran indicates that the auto-microfluidics CPA exchange protocol induces less cytoplasmic leakage and membrane damage. These results are consistent with the result that more rapid membrane compression and associated buckling cause more transient membrane damage to allow impermeable solute intercalation.

Increased Developmental Competence.

To analyze how shrinkage rates affect embryo developmental competence, the number of blastomeres per blastocyst after 96 h culture were assessed using NCEV murine zygotes as control and zygotes vitrified with manual-pipetting and auto-microfluidic CPA exchange as the experimental groups. NCEV zygotes have 109±4 blastomeres (n=46) after 96 h embryo development. Both CPA exposure/vitrification methods caused sub-lethal damage that significantly reduced blastomeres per blastocyst verses NCEV control. Furthermore, the vitrification method with the faster shrinkage rate (manual-pipetting) resulted in significantly less blastomeres per blastocyst (89±3 blastomeres, n=35) compared to the method with reduced shrinkage rate (auto-microfluidic; 98±3 blastomeres, n=46, $p<0.05$). Thus, sub-lethal damage was significantly decreased using vitrification by auto-microfluidic CPA exposure which preserved zygotes with higher developmental competence compared to its manual-pipetting counterpart (FIG. 4C).

This example describes how a slow and steady cell shrinkage rate during cryoprotectant agent (CPA) exchange reduces sub-lethal cellular damage. A user-friendly and precise microfluidic CPA exchange system that significantly reduces the variability in terms of fluid exchange timing, volume error as well as convective forces applied to cells was developed. This contrasts with commonly-used pipetting-based manual CPA exchange protocols that are difficult to reproduce exactly, even within a single operator, resulting in cryopreservation outcome variability (Tsang and Chow, *Birth Defects Res Part C Embryo Today Rev* 2010; 90:163-175). By eliminating run-to-run and operator-to-operator variability, the automated microfluidic system is broadly useful in the discovery, validation, and use of new CPA formulation and procedures. As a consideration for potential clinical use of the device, it is noted that the microfluidic cell introduction and recovery rate for 462 oocytes and zygotes has been 100%. The benefits observed from the gradient CPA exchange are also advantageous to an automated warming process post-vitrification.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

We claim:

1. A microfluidic device for the cryopreservation of a biological material, comprising:
    a cryoprotectant solution input;
    a culture medium input;
    a serpentine mixing channel in fluid communication with the cryoprotectant solution input and the culture medium input;
    a housing chamber in fluid communication with the serpentine mixing channel;
    a port coupled to the housing chamber and configured to provide access for loading and unloading of biological material into the housing chamber; and
    a plurality of height-differential negative pressure holding channels each in fluid communication with the housing chamber, wherein the plurality of height-differential negative pressure holding channels is configured to maintain the biological material in the housing chamber when subjected to a constant volumetric flow of fluid of changing fluid density through the housing chamber.

2. The microfluidic device of claim 1 further comprising a vitrification solution.

3. The microfluidic device of claim 1 further comprising a cryoprotectant agent having a concentration that changes as a function of time.

4. The microfluidic device of claim 1 further comprising a biological material that is to be cryopreserved.

5. The microfluidic device of claim 1 wherein the biological material is an oocyte, a zygote, a stem cell, an embryo, an ovarian follicle, a embryoid body, an organoid, or a tissue.

6. The microfluidic device of claim 1 wherein the biological material is from a human.

7. The microfluidic device of claim 1 wherein the biological material is from a human having cancer or infertility.

8. The microfluidic device of claim 1 comprising polydimethylsiloxane.

9. The microfluidic device of claim 1 wherein the vitrification solution comprises an impermeable solute.

10. A system for the cryopreservation of a biological material, the system comprising:
    a) a device according to claim 1;
    b) a cyroprotectant solution comprising a cryoprotectant agent;
    c) a syringe pump in operable fluidic communication with the cyroprotectant solution input;
    d) a syringe pump in operable fluidic communication with the culture medium input;
    e) a thermodynamic heat pump to remove heat from the device and freeze biological material contained therein.

11. The system of claim 10 further comprising a microchip configured to perform instructions to control the syringe pump in operable fluidic communication with the cyroprotectant solution input and to control the syringe pump in operable fluidic communication with the culture medium input.

12. The system of claim 10 wherein a rate of delivery of the cyroprotectant solution is controllable and the rate of delivery of a culture medium is controllable.

13. The system of claim 10 wherein the cyroprotectant solution comprises an impermeable solute.

14. The system of claim 10 wherein the syringe pump in operable fluidic communication with the cyroprotectant solution input and the syringe pump in operable fluidic communication with the culture medium input provide a vitrification solution comprising a time-dependent concentration of the cryoprotectant agent.

15. The microfluidic system of claim 10, wherein the plurality of height-differential negative pressure holding channels each have a negative height differential that generates suction in the housing chamber in an absence of syringe pump flow.

* * * * *